United States Patent
Tearney et al.

(10) Patent No.: US 11,963,661 B2
(45) Date of Patent: *Apr. 23, 2024

(54) SYSTEMS, METHODS, AND MEDIA FOR CAPSULE-BASED MULTIMODE ENDOSCOPY

(71) Applicant: The General Hospital Corporation, Boston, MA (US)

(72) Inventors: Guillermo J. Tearney, Cambridge, MA (US); Kanwarpal Singh, Weymouth, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/067,566

(22) Filed: Dec. 16, 2022

(65) Prior Publication Data
US 2023/0117240 A1    Apr. 20, 2023

Related U.S. Application Data

(63) Continuation of application No. 17/052,438, filed as application No. PCT/US2019/030699 on May 3, 2019, now Pat. No. 11,534,058.
(Continued)

(51) Int. Cl.
*A61B 1/00* (2006.01)
*A61B 1/01* (2006.01)
(Continued)

(52) U.S. Cl.
CPC ............ *A61B 1/00096* (2013.01); *A61B 1/01* (2013.01); *A61B 1/041* (2013.01); *A61B 1/07* (2013.01)

(58) Field of Classification Search
CPC ..... A61B 1/041; A61B 1/0638; A61B 5/0035; A61B 5/0066; A61B 1/00172; G02B 6/262; G02B 6/32; G02B 6/34
See application file for complete search history.

(56) References Cited

U.S. PATENT DOCUMENTS 5,307,146 A    4/1994  Porter
5,582,171 A *  12/1996 Chornenky ........... A61M 25/09
                                                600/479
(Continued)

FOREIGN PATENT DOCUMENTS

CN    105526883 A    4/2016
WO    2006014392 A1  2/2006
WO    2017059246 A1  4/2017

OTHER PUBLICATIONS

International Searching Authority. International Search Report and Written Opinion for application PCT/US2019/030699, dated Jul. 12, 2019. 13 pages.

*Primary Examiner* — Aaron B Fairchild
*Assistant Examiner* — Stephen Floyd London
(74) *Attorney, Agent, or Firm* — Quarles & Brady LLP

(57) ABSTRACT

In some embodiments, systems, methods, and media for capsule-based multimode endoscopy are provided. In some embodiments, a probe for capsule-based multimode endoscopy is provided, the probe comprising: a rigid capsule; a flexible tether coupled to a proximal end of the capsule; a rotatable reflective surface disposed within the capsule; a static ball lens disposed within the capsule; a first optical fiber optically coupled to the ball lens, the first optical fiber passing through the flexible tether; a second optical fiber optically coupled to the ball lens, the second optical fiber passing through the flexible tether; a graded index fiber disposed between a distal end of the second optical fiber and
(Continued)

the ball lens, the graded index fiber optically coupled to the second optical fiber and the ball lens.

28 Claims, 12 Drawing Sheets

Related U.S. Application Data

(60) Provisional application No. 62/666,660, filed on May 3, 2018.

(51) Int. Cl.
*A61B 1/04* (2006.01)
*A61B 1/07* (2006.01)

(56) References Cited

U.S. PATENT DOCUMENTS

| | | |
|---|---|---|
| 5,910,839 A | 6/1999 | Erskine |
| 6,430,337 B1 | 8/2002 | Bergmann |
| 6,445,939 B1 | 9/2002 | Swanson |
| 6,485,413 B1 | 11/2002 | Boppart |
| 6,975,898 B2 | 12/2005 | Seibel |
| 7,530,948 B2 | 5/2009 | Seibel |
| 8,035,819 B2 | 10/2011 | Zuluaga |
| 8,432,542 B2 | 4/2013 | Marple |
| 8,914,098 B2 | 12/2014 | Brennan |
| 9,451,885 B2 | 9/2016 | Liu |
| 9,557,154 B2 | 1/2017 | Tearney |
| 2003/0081897 A1 | 5/2003 | Itoh |
| 2006/0067620 A1 | 3/2006 | Shishkov |
| 2007/0038120 A1* | 2/2007 | Richards-Kortum ................. A61B 5/444 600/476 |
| 2007/0188855 A1 | 8/2007 | Shishkov |
| 2008/0058629 A1 | 3/2008 | Seibel |
| 2008/0267562 A1* | 10/2008 | Wang ................. G02B 26/108 362/572 |
| 2009/0185191 A1 | 7/2009 | Boppart |
| 2009/0244545 A1 | 10/2009 | Toida |
| 2009/0323076 A1* | 12/2009 | Li ................. G01B 9/02063 356/479 |
| 2011/0262072 A1 | 10/2011 | Lewis |
| 2012/0101390 A1 | 4/2012 | Iftimia |
| 2013/0266259 A1* | 10/2013 | Bhagavatula ........ G01B 9/0205 385/33 |
| 2013/0310643 A1 | 11/2013 | Gora |
| 2014/0153864 A1* | 6/2014 | Sinclair ............... A61B 5/0084 385/12 |
| 2014/0285810 A1* | 9/2014 | Vacas ................ G01B 9/02091 356/479 |
| 2014/0288368 A1 | 9/2014 | Hendriks |
| 2014/0309527 A1* | 10/2014 | Namati ................ A61B 5/0073 600/407 |
| 2014/0378846 A1 | 12/2014 | Hosoda |
| 2016/0206373 A1* | 7/2016 | Chen ................... A61B 5/0084 |
| 2016/0227990 A1* | 8/2016 | Li ........................ A61B 5/0066 |
| 2016/0242737 A1 | 8/2016 | Zhou |
| 2016/0357007 A1* | 12/2016 | Swanson ............ G01B 9/02028 |
| 2017/0135584 A1 | 5/2017 | Tearney |
| 2017/0143196 A1 | 5/2017 | Liang |
| 2018/0014773 A1 | 1/2018 | Barton |
| 2018/0160965 A1 | 6/2018 | Tearney |
| 2018/0303327 A1 | 10/2018 | Yamada |
| 2019/0099079 A1 | 4/2019 | Yamada |
| 2019/0104941 A1* | 4/2019 | Yamamoto ........... A61B 5/0062 |
| 2019/0212761 A1 | 7/2019 | Swanson |
| 2019/0374092 A1 | 12/2019 | Wu |
| 2019/0374196 A1* | 12/2019 | Courtney ............. A61B 5/0066 |
| 2020/0000327 A1 | 1/2020 | Li |
| 2020/0093365 A1* | 3/2020 | Wu ........................ A61B 5/0084 |
| 2020/0129068 A1 | 4/2020 | Fan |
| 2021/0109340 A1* | 4/2021 | Liang ................. A61B 1/00177 |

\* cited by examiner

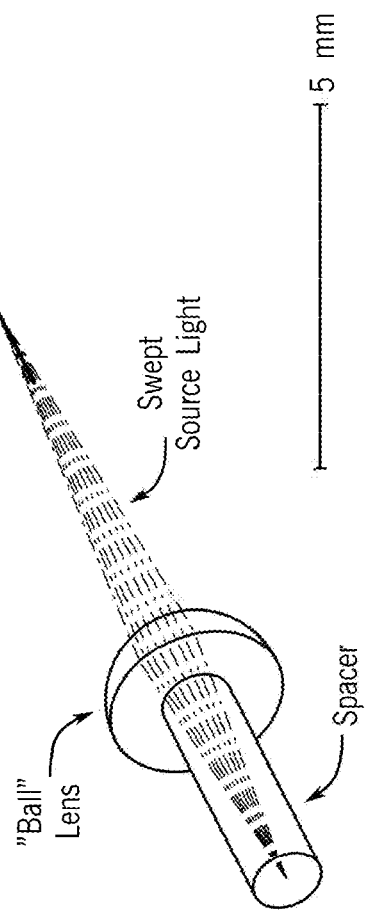
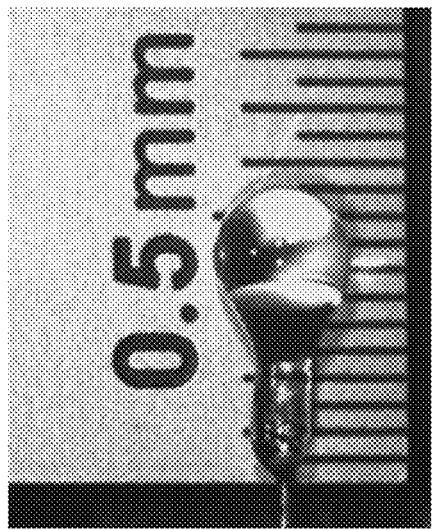
FIG. 3B
FIG. 3C

Visible Light Spot size at the same scale — lower resolution, larger depth of focus OCT Light Spot size — higher resolution, smaller depth of focus

SYSTEMS, METHODS, AND MEDIA FOR CAPSULE-BASED MULTIMODE ENDOSCOPY

CROSS-REFERENCE TO RELATED APPLICATIONS

This application is a continuation of U.S. patent application Ser. No. 17/052,438, filed Nov. 2, 2020, which is a National Stage of International Application No. PCT/US2019/030699, filed May 3, 2019, which is based on, claims the benefit of, and claims priority to U.S. Provisional Application No. 62/666,660, filed May 3, 2018, and entitled "TETHERED CAPSULE ENDOSCOPE ENDOMICROSCOPE." The contents of each of these applications are hereby incorporated herein by reference in their entirety for all purposes.

STATEMENT REGARDING FEDERALLY SPONSORED RESEARCH

N/A

BACKGROUND

Gastrointestinal (GI) diseases are one of the most commonly reported health care issues and a major contributor to the health care burden within Unites States and worldwide. According to recent studies, there were approximately 60 million ambulatory visits related to digestive disorders, while GI-related healthcare costs are estimated to be upwards of $140 billion annually. Endoscopy is often the primary diagnostic tool used in the GI tract, and must be performed under anesthesia using conventional endoscopy techniques. Endoscopy is a major contributor to GI-related healthcare costs disease burden is endoscopy which. In 2012, an estimated 6.9 million upper GI endoscopies were performed with an estimated cost of $12.3 billion. The scale and impact of GI disorders on health care and health care costs are driving development of new technologies to aid standard white light imaging (WLI)-based endoscopy to better diagnose GI diseases, some of which can be performed without sedating the subject via anesthesia. Optical coherence tomography (OCT) has emerged a promising tool in this direction which provides real time volumetric images of the whole GI tract at microscopic (e.g., on the order of 30×30×10 micrometers (μm)) resolution compared to conventional WLI-based endoscopy which only provides luminal surface images at a macroscopic level, which omits details of the underlying tissue. However, while OCT can provide microscopic information about the structure of the tissue without anesthesia (e.g., via tethered capsule OCT techniques), conventional OCT techniques cannot be used to generate visible light images of the surface of the tissue. Such visible light images, which are generated via conventional WLI endoscopy, can often provide more useful information than OCT for diagnosing certain conditions such as esophagitis, strictures, and/or ulcers.

Accordingly, devices, systems, and methods for capsule-based multimode endoscopy are desirable.

SUMMARY

In accordance with some embodiments of the disclosed subject matter, devices, systems, and methods for capsule-based multimode endoscopy are provided.

In accordance with some embodiments of the disclosed subject matter, a probe is provided, the probe comprising: a rigid capsule; a flexible tether coupled to a proximal end of the capsule; a rotatable reflective surface disposed within the capsule; a static ball lens disposed within the capsule; a first optical fiber optically coupled to the ball lens, the first optical fiber passing through the flexible tether; a second optical fiber optically coupled to the ball lens, the second optical fiber passing through the flexible tether; and a graded index fiber disposed between a distal end of the second optical fiber and the ball lens, the graded index fiber optically coupled to the second optical fiber and the ball lens.

In some embodiments, the rotatable reflective surface is configured to receive light emitted by the ball lens and direct the light toward a circumference of the rigid capsule.

In some embodiments, the probe further comprises a spacer disposed between the ball lens and the graded index fiber.

In some embodiments, the first optical fiber is a single mode fiber that is configured to be optically coupled to an optical coherence tomography imaging system.

In some embodiments, the second optical fiber is a dual clad fiber that is configured to be optically coupled to a visible light imaging system.

In some embodiments, the graded index fiber has a length of between 100 and 1,000 micrometers (μm).

In some embodiments, the ball lens has an axial diameter of between 0.1 and 5 millimeters (mm).

In some embodiments, the probe further comprises a motor that is mechanically coupled to the rotatable reflective surface, and configured to rotate the rotatable reflective surface.

In accordance with some embodiments of the disclosed subject matter, a system for capsule-based multimode endoscopy is provided, the system comprising: a visible light imaging system comprising: a visible light source; and a visible light detector; an optical coherence tomography (OCT) imaging system comprising: an OCT light source; an OCT detector; a sample arm optically coupled to the OCT light source and the OCT detector; and a reference arm optically coupled to the OCT light source and the OCT detector, the reference arm comprising a reference reflector; and a probe comprising: a rigid capsule; a flexible tether coupled to a proximal end of the capsule; a rotatable reflective surface disposed within the capsule; a static ball lens disposed within the capsule; a first optical fiber optically coupled to the ball lens and the sample arm of the OCT imaging system, the first optical fiber passing through the flexible tether; a second optical fiber optically coupled to the ball lens and the visible light imaging system, the second optical fiber passing through the flexible tether; and a graded index fiber disposed between a distal end of the second optical fiber and the ball lens, the graded index fiber optically coupled to the second optical fiber and the ball lens.

In some embodiments, the system further comprises: at least one processor that is programmed to: cause the rotatable reflective surface to rotate; cause the OCT light source to emit light toward the rotatable reflective surface via the first optical fiber; cause the visible light source to emit light toward the rotatable reflective surface via the second optical fiber; generate OCT data based on an interference between light reflected from a sample and light reflected from the reference reflector; generate visible light image data based on light reflected from a surface of the sample; and cause an image representing a first portion of the sample based on the OCT data to be presented simultaneously with an image representing the first portion of the sample based on the visible light image data.

In some embodiments, the rotatable reflective surface is configured to receive light emitted by the ball lens and direct the light toward a circumference of the rigid capsule.

In some embodiments, the probe further comprises a spacer disposed between the ball lens and the graded index fiber.

In some embodiments, the first optical fiber is a single mode fiber.

In some embodiments, the second optical fiber is a dual clad fiber, the core of the dual clad fiber optically coupled to the visible light source and the cladding of the dual clad fiber optically coupled to the visible light detector.

In some embodiments, the graded index fiber has a length of between 100 and 1,000 µm.

In some embodiments, the ball lens has an axial diameter of between 0.1 and 5 mm.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

FIG. 3B shows an example of optical components that can be used to focus light from an OCT light source and a visible light source at a similar focal length implemented in accordance with some embodiments of the disclosed subject matter.

FIG. 3C shows an example simulation of optical paths of light from an OCT light source and a visible light source emitted from optics implemented in accordance with some embodiments of the disclosed subject matter.

DETAILED DESCRIPTION

In accordance with some embodiments of the disclosed subject matter, mechanisms (which can include devices, systems, and methods) for capsule-based multimode endoscopy are provided.

In accordance with some embodiments of the disclosed subject matter, mechanisms for generating OCT and visible light image data substantially simultaneously can be provided. In some embodiments, such mechanisms can reduce a subject's discomfort, reduce procedure time, and facilitate post procedure image co-registration for OCT and visible light images. Previous attempts have been made to combine a mini color camera along and rotating OCT optics inside a tethered capsule. However, this arrangement suffers from complications such as non-uniform rotational distortion in the OCT data, and a mismatch in perspective between a forward-facing color camera and the circumferential OCT imaging modality, which cause difficulties co-registering images obtained with both modalities. In some embodiments, the mechanisms described herein can facilitate generation of OCT and visible light images (e.g., of the upper GI tract) that feature a similar perspective and can more easily be spatially and temporally co-registered.

Figure 1:
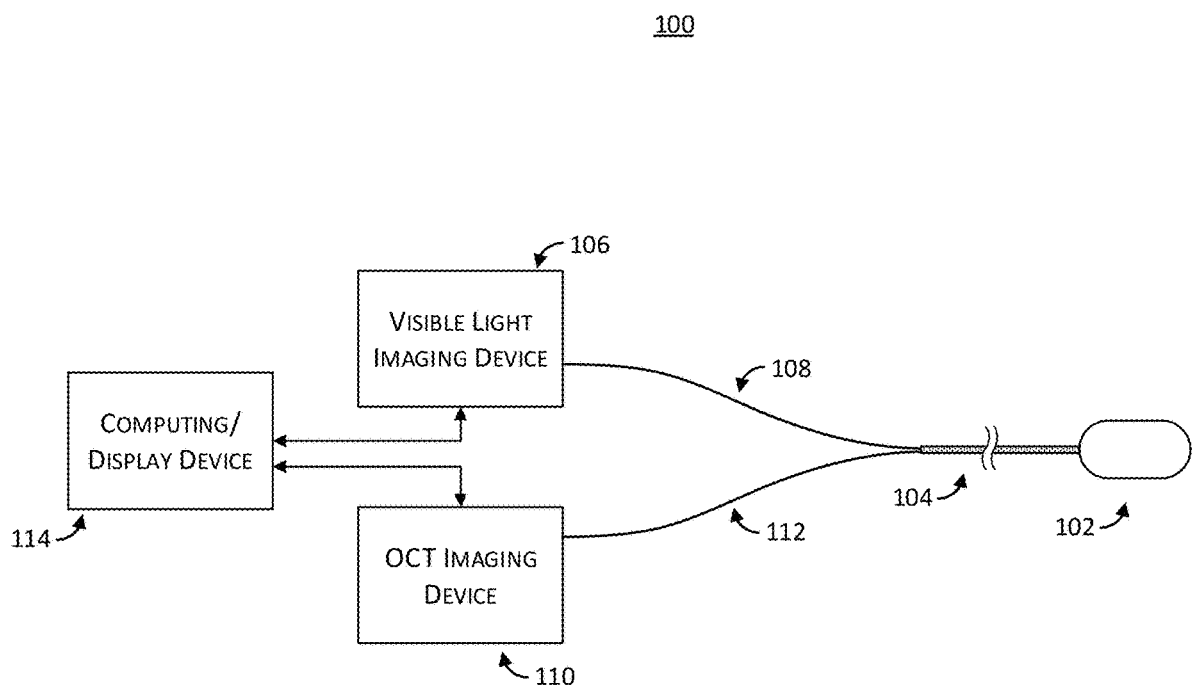
FIG. 1 shows an example of a system for capsule-based multimode endoscopy in accordance with some embodiments of the disclosed subject matter.

FIG. 1 shows an example 100 of a system for capsule-based multimode endoscopy in accordance with some embodiments of the disclosed subject matter. As shown in FIG. 1, system 100 can include a capsule 102 mechanically coupled to a tether 104. As described below in connection with FIGS. 3A, and 4A to 4C, capsule 102 can include optical components that are configured to direct light received via tether 104 toward a circumference of capsule 102, such that the light is directed toward a surface of a subject's organ, such as the esophagus or another portion of the subject's GI tract.

In some embodiments, a visible light imaging device 106 can be optically coupled to capsule 102 via an optical waveguide 108 (e.g., an optical fiber). In some embodiments, visible light imaging device 106 can emit visible light at one or more wavelengths toward a proximal end of optical waveguide 108, which can convey the visible light to one or more optical components in capsule 102. In some embodiments, the one or more optical components in capsule 102 can cause the visible light to be directed toward a circumference of capsule 102 and onto a surface of a subject's organ (e.g., after the subject has swallowed capsule 102). A portion of the visible light can be reflected by the surface of the subject's organ back toward capsule 102. In some embodiments, one or more optical components in capsule 102 can direct the reflected light back toward a distal end of optical waveguide 108, which can convey the reflected light back to visible light imaging device 106. In some embodiments, visible light imaging device 106 can include one or more detectors that can be used to detect visible light returned from capsule 102, and one or more processors (e.g., included in visible light imaging device or in another device) can generate visible light image data based on the visible light detected by visible light imaging device.

In some embodiments, an OCT imaging device 110 can be can be optically coupled to capsule 102 via an optical waveguide 112 (e.g., an optical fiber). In some embodiments, OCT imaging device 110 can emit light at one or more wavelengths suitable or OCT imaging (e.g., infrared light, near-infrared light) toward a proximal end of optical waveguide 112, which can convey the light to one or more optical components in capsule 102. In some embodiments, the one or more optical components in capsule 102 can cause the light to be directed toward a circumference of capsule 102 and toward a surface of a subject's organ (e.g., after the subject has swallowed capsule 102). A portion of the light can be reflected at various depths from the surface of the subject's organ to several millimeters (e.g., on the order of 3-4 mm) below the surface of the subject's organ back toward capsule 102. In some embodiments, one or more optical components in capsule 102 can direct the reflected OCT light back toward a distal end of optical waveguide 112, which can convey the reflected OCT light back to OCT imaging device 110. In some embodiments, OCT imaging device 110 can include one or more detectors that can be used to detect OCT light returned from capsule 102, and one or more processors (e.g., included in visible light imaging device or in another device) can generate OCT image data based on the visible light detected by visible light imaging device 106. As described below in connection with FIG. 2, a portion of the light emitted by OCT imaging device 110 can be directed to a reference arm with a reflector that is positioned at approximately the same distance from the one or more detectors as the sample (e.g., the surface of the subject's organ) to be imaged.

In some embodiments, a computing device 114 can be coupled to visible light imaging device 106 and/or OCT imaging device 110, and can be configured to process, display, and/or store image data generated by visible light imaging device 106 and/or OCT imaging device 110 in real time. In some embodiments, computing device 114 can control and/or coordinate operation of visible light imaging device 106 and/or OCT imaging device 110. In some embodiments, computing device 114 can be configured to communicate with visible light imaging device 106 and/or OCT imaging device 110 using any suitable technique or combination of techniques, such as via wired links (e.g., Ethernet, USB, etc.) and/or wireless links (e.g., Wi-Fi, Bluetooth, etc.).

Figure 2:
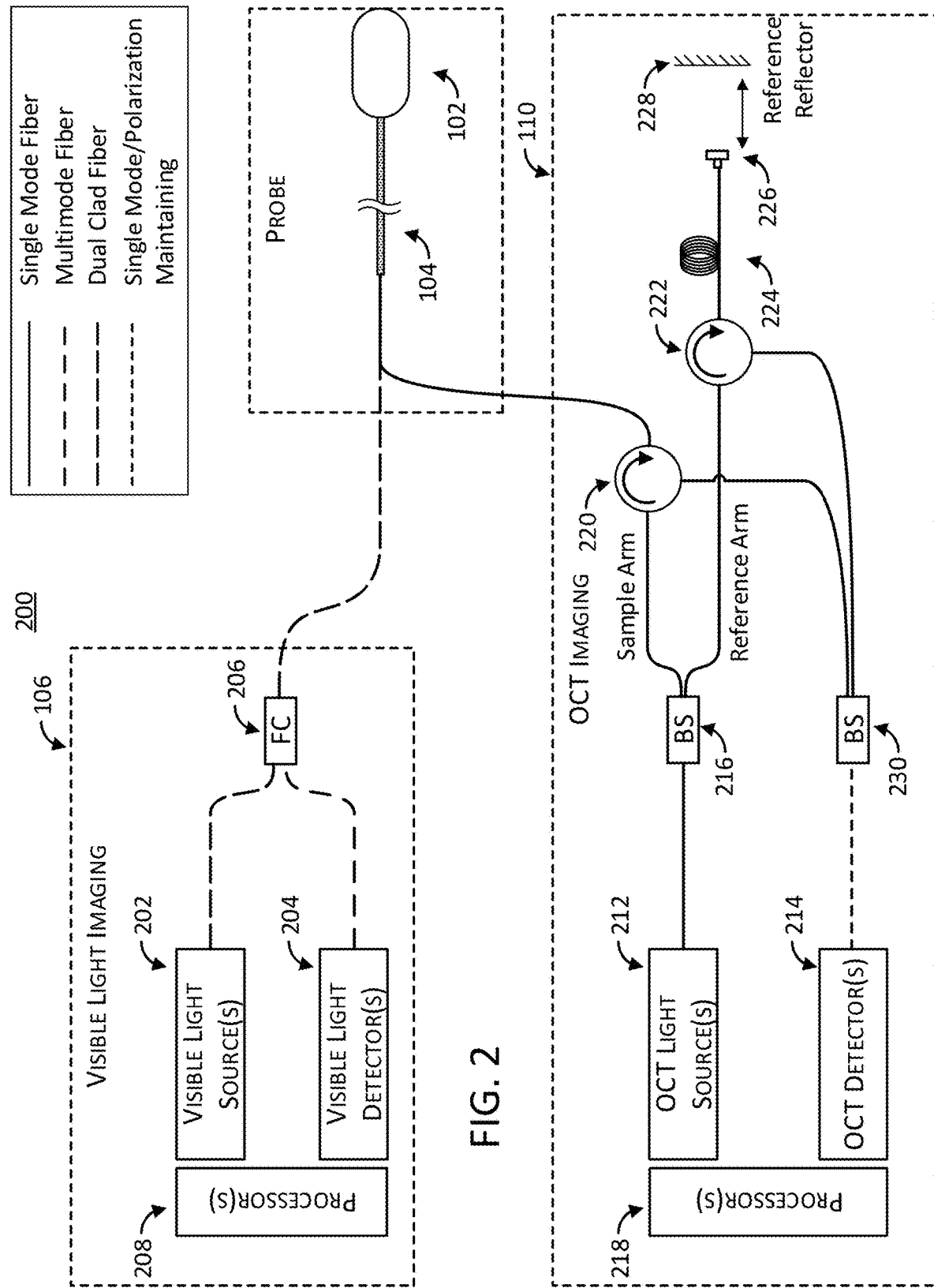
FIG. 2 shows an example of a components that can be used to implement a system for capsule-based multimode endoscopy in accordance with some embodiments of the disclosed subject matter.

FIG. 2 shows an example 200 of a components that can be used to implement a system for capsule-based multimode endoscopy in accordance with some embodiments of the disclosed subject matter. As shown in FIG. 2, visible light imaging device 106 can include one or more visible light sources 202 and one or more visible light detectors 204, each optically coupled to a fiber coupler 206 (e.g., a dual clad fiber coupler), in some embodiments. In some embodiments, visible light source(s) 202 can be optically coupled to a port of fiber coupler 206 using a dual clad fiber, and visible light detector(s) 204 can be optically coupled with a second port of fiber coupler 206 using an optical fiber (e.g., a single mode fiber, dual clad fiber, or a multimode fiber). In one particular example, a multimode fiber can be fused to a dual clad fiber provided at a port of the fiber coupler 206. In some embodiments, a dual clad fiber (sometimes referred to as a double clad fiber) can be used to optically couple a third port of fiber coupler 206 with one or more optical components within probe 102 (e.g., as described below in connection with FIG. 3A). Note that, in some embodiments, an optical circulator can be used in lieu of fiber coupler 206, with a first port optically coupled to visible light source(s) 202, a second port optically coupled to one or more optical components within capsule 102, and a third port optically coupled to visible light detector(s) 204.

In some embodiments, one or more processors 208 can be electrically coupled to visible light source(s) 202 and/or visible light detector(s) 204, and can be configured to control operation of visible light source(s) 202, visible light detector(s) 204, and/or any other components of visible light imaging device 106. Additionally, in some embodiments, processor 208 can be configured to process and/or output image data generated using visible light detector(s) 204.

In some embodiments, visible light source(s) 202 can be any suitable light source that can be used to generate visible light image data. For example, in some embodiments, visible light source(s) 202 can be implemented using a broadband white light source. In some embodiments, any suitable light source or combination of light sources can be used to implement visible light source(s) 202, such as a filament-based light source, one or more conventional light emitting diodes (LEDs), one or more superluminescent LEDs (SLED), one or more superluminescent diodes (SLD), one or more plasma light sources, one or more supercontinuum light sources, one or more femtosecond lasers. As another example, visible light source(s) 202 can be implemented using multiple visible light sources, such as a green light source, a red light source, and a blue light source, which can be activated simultaneously or intermittently. In a more particular example, a first light source (e.g., a green light source) can be activated for a period of time corresponding to a particular number of revolutions of optics within capsule 102, a second light source (e.g., a red light source) can be activated for a period of time corresponding to a successive particular number of revolutions of optics within capsule 102, and so on.

In some embodiments, visible light detector(s) 204 can be any suitable visible light detector(s) that can be used to generate visible light image data. For example, in some embodiments, visible light detector(s) 204 can be implemented using a CCD or CMOS sensor that receives light reflected from the sample (e.g., via a multimode fiber optically coupled to fiber coupler 206), and converts the reflected light into image data. In some embodiments, visible light detector(s) 204 can include an array of detector elements (e.g., a linear array of pixels, a two dimensional array of pixels), and one or more optical components can be used to cause light reflected from the sample to be directed to different portions of the array. For example, the reflected light can be spread across the array using a negative lens that receives light emitted from an optical fiber and cause the received light to diverge from the lens. In such an example, different pixels in the array can be associated with filters having different wavelengths such that the amount of light reflected from the sample at each of the different wavelengths can be measured. As another example, the reflected light can be spread across the array using a grating or other spectral dispersion element (e.g., a prism) that directs different wavelengths of light toward different portions of the array. In such an example, different pixels in the array can be associated with different wavelengths based on the spatial relationship between the position of the pixel and the spectral dispersion element such that the amount of light reflected from the sample at each of the different wavelengths can be measured. As yet another example, the reflected light can be input to a fiber-based wavelength division multiplexor (WMD) that outputs light at different wavelengths from different optical fibers. In such an example, different pixels in the array can be associated with different optical fibers, and hence different wavelengths, such that the amount of light reflected from the sample at each of the different wavelengths can be measured. As another example, visible light detector(s) 204 can be implemented using one or more monochromatic visible light pixels (e.g., having an IR cut filter, but not having a color filter) configured to detect light that returns to visible light detector(s). In such an example, visible light source(s) 202 can be configured to output a single color for a particular period of time, and processor 208 can assign color information to the image data based on the time at which the image data was generated.

In some embodiments, OCT imaging device 110 can include one or more OCT light source(s) 212 and one or more OCT detector(s) 214. In some embodiments, OCT light source(s) 202 can be optically coupled to a port of a beam splitter 216 using a single mode fiber, and output ports of beam splitter 216 can each be optically coupled to a first port of optical circulators 220 and 222 using single mode fibers. In some embodiments, beam splitter 216 can direct any suitable portion of the light received from OCT light source(s) 212 toward the sample arm and reference arm. For example, beam splitter 216 can direct 90% if the light received from OCT light source(s) 212 toward the sample arm and 10% toward the reference arm.

In some embodiments, optical circulator 220 can be integrated into a sample arm, in which a second port of optical circulator 220 is optically coupled to one or more optical components in capsule 102 via a single mode fiber, which can convey light emitted by OCT light source(s) 212 to capsule 102 and convey light from a sample back from capsule 102 to the second port of optical circulator 220.

In some embodiments, optical circulator 222 can be integrated into a reference arm, in which a second port of optical circulator 222 is optically coupled via a length of optic waveguide 224 (e.g., single mode fiber) that can be configured to delay light from optical circulator 222 such that the length of the reference arm is substantially similar to a length of the sample arm (e.g., similar on the order of the ranging depth, such as from 0 to 10 mm). In some embodiments, optics 226 can be used to direct a beam of light toward a reference reflector 228, and to collect light reflected from reference reflector 228. In some embodiments, optics 226 and/or reference reflector can be actuated to change the length of the reference arm.

In some embodiments, light reflected by the sample can be received at the second port of optical circulator 220 and light reflected by reference reflector 228 can be received at the second port of optical circulator 222, and the third port of each optical circulator 220 and 222 can be optically coupled to a beam splitter 230, that is optically coupled to one or more OCT detector(s) 214.

In some embodiments, one or more processors 218 can be electrically coupled to OCT light source(s) 212 and/or OCT detector(s) 214, and can be configured to control operation of OCT light source(s) 212, OCT detector(s) 214, and/or any other components of OCT imaging device 110. Additionally, in some embodiments, processor 218 can be configured to process and/or output OCT data generated using OCT detector(s) 214.

In some embodiments, OCT light source(s) 212 can be any suitable light source that can be used to generate OCT data. For example, in some embodiments, OCT light source(s) 212 can be implemented using a swept source laser. As another example, a polychromatic light source can be used to implement OCT light source(s) 212. As yet another example, a broadband light source can be used to implement OCT light source(s) 212. As still another example, a frequency comb light source can be used to implement OCT light source(s) 212. Note that different OCT imaging techniques can be used for different types of light source. For example, optical frequency domain imaging (OFDI) OCT techniques can be used with a swept source, while spectral-domain OCT (SD-OCT) techniques can be used with a frequency comb source. In a more particular example, OCT light source(s) 212 can be implemented using a Swept Source Engine from AXSUN Technologies (of Billerica, Massachusetts), which can include a swept laser that sweeps over a range of about 50-200 nm (e.g., a range of 50 nm, 75 nm, 100 nm, 125 nm, 150 nm, 175 nm, 200 nm, or any other suitable range) centered in the infrared or near infrared (e.g., 850 nm, 1060 nm, 1220 nm, 1310 nm, 1700 nm, or any other suitable wavelength) at a frequency of about 50 kilohertz (kHz) to 200 kHz (e.g., 50 kHz, 75 kHz, 100 kHz, 125 kHz, 150 kHz, 175 kHz, 200 kHz, or any other suitable frequency). In some embodiments, the spectral width can be on the order of 0.1 to 1 angstrom.

In some embodiments, OCT detector(s) 214 can be any suitable detector(s) that can be used to generate OCT data. For example, in some embodiments, OCT detector(s) 214 can be implemented using one or more CCD or CMOS sensors that receive light reflected from the sample (e.g., via one or more single mode fibers optically coupled to beam splitter 230), and convert the reflected light into OCT data. In some embodiments, sample and reference signals interfere with each other at beam splitter 230. In some such embodiments, multiple outputs of beam splitter 230 can each be coupled to a polarization beam splitter via a single mode fiber coupled to one or more polarization controllers and polarization maintaining fiber to implement a polarization diverse detection scheme that can avoid image artifacts due to polarization changes induced by the optical fiber in catheter 104. In some embodiments, light from the polarization maintaining fibers can be detected using two balanced detectors composed of four photodiode receivers (e.g., each supplied by an output of a polarization beam splitter). The digitized signal from the photodiodes can then be processed using a field-programmable gate array (FPGA)

or application specific integrated circuit (ASIC) board including wavelength re-mapping and Fourier transformation to obtain a depth-resolved OCT signal (sometimes referred to as an A-line). In some embodiments, regardless of how the A-lines are generated, the A-lines can be collected during every rotation of the optical beam and compressed to a jpeg format and transferred using an Ethernet cable to a workstation (e.g., computing device 114), for real-time display and/or data storage. Note that this is merely an example, and other detection techniques and/or processing techniques can be used to generate OCT data. For example, a single detector can be used to detect an interference pattern between light from the sample arm and the reference arm. As another example, one or more common path interferometry techniques in which the reference arm and sample arm travel substantially the same path (e.g. the reference reflector can be located within capsule 102). As yet another example, one or more polarization diversity detection techniques can be used. As still another example, one or more SD-OCT techniques can be used in which different pixels in the detection array are configured to detect light at a different wavelength (e.g., light can be directed across the array using a spectral dispersion element). In some embodiments, one or more filters can be used to inhibit OCT light from reaching visible light detector(s) and vice versa. For example, bulk optical filters can be used to inhibit light in unwanted wavelengths from reaching the detectors. As another example, a fiber-based WMD can be used to divert light at an undesirable wavelength(s) from reaching the detector(s).

Figure 3A:
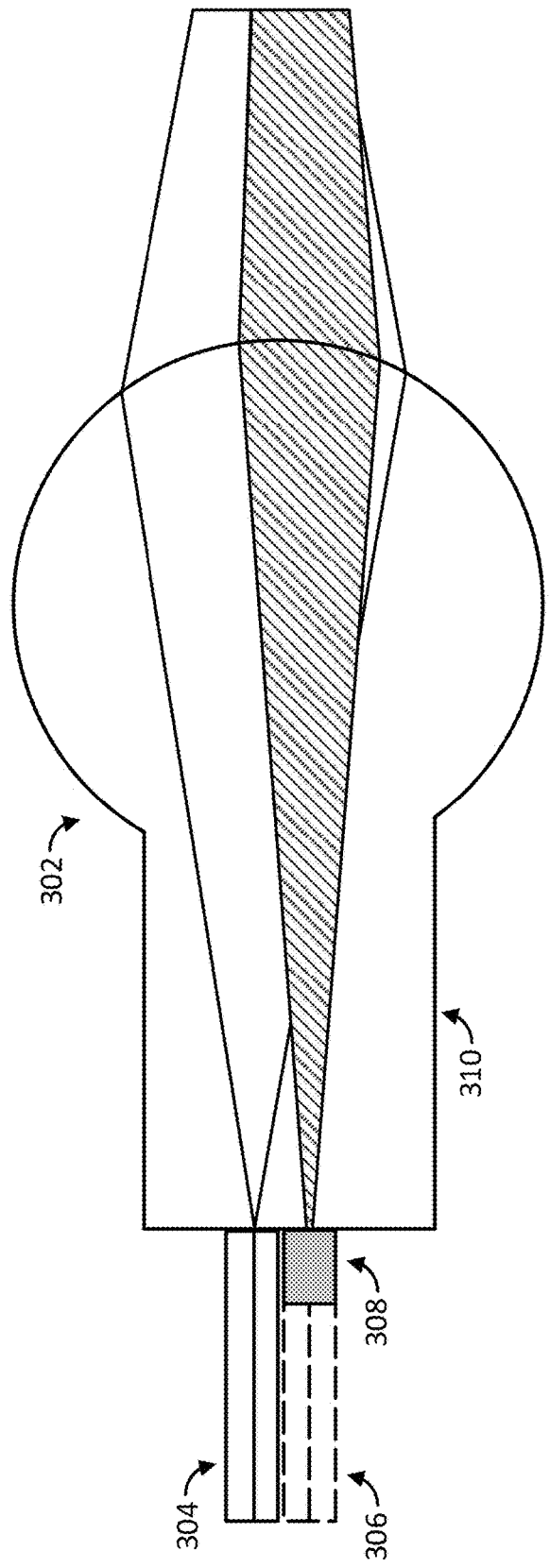
FIG. 3A shows an example of optical components that can be used to focus light from an OCT light source and a visible light source at a similar focal length to implement a portion of a system for capsule-based multimode endoscopy in accordance with some embodiments of the disclosed subject matter.

FIG. 3A shows an example 300 of optical components that can be used to focus light from an OCT light source and a visible light source at a similar focal length to implement a portion of a system for capsule-based multimode endoscopy in accordance with some embodiments of the disclosed subject matter. As shown in FIG. 3A, one or more optical components can be used to focus light emitted by one or more visible light sources (e.g., visible light source(s) 202) and/or one or more OCT light sources (e.g., OCT light source(s) 212). In some embodiments, optics 300 can include a ball lens 302 that can be optically coupled to an OCT light source(s) via a single mode fiber 304. Note that this is merely an example, and other suitable types of focusing elements or combination of elements can be used such as a gradient-index (GRIN) lens, an aspheric lens, a Fresnel lens, etc. For example, single mode fiber 304 can have a diameter of roughly 125 μm (e.g., the conventional cladding can have an external diameter of roughly 125 μm surrounding a core having a diameter in the range of about 4 to 10 μm, although the cladding can have other diameters, such as in the range of 60-250 μm). Additionally, in some embodiments, ball lens 302 can be optically coupled to a visible light source(s) via a dual clad fiber 306 and a portion of graded index (GRIN) fiber 308 that can serve to narrow the beam of visible light emitted by dual clad fiber 306. For example, dual clad fiber 306 can have a diameter of roughly 125 μm. (e.g., the outer layer of cladding can have an external diameter of roughly 125 μm surrounding an inner layer of cladding and a core having a diameter in the range of about 4 to 10 μm, although the outer cladding can have other diameters, such as in the range of 60-250 μm) As another example, GRIN fiber 308 can have a length in the range of about 0.1 to 5 mm (e.g., a length of about 100 μm, 150 μm, 200 μm, 250 μm, etc.) or longer (e.g., a maximum rigid length of the probe, such as 1 centimeter). Note that the GRIN fiber can confine the signal, and can be configured to have a length that causes the visible light to exit the GRIN fiber with a beam width that will cause an appropriate beam size at the surface of the sample (e.g., to provide an appropriate lateral resolution for color imaging). In some embodiments, various factors can be considered when setting the length of the GRIN lens, such as the index of refraction of the focusing element (e.g., the material used to make a ball lens that is used to focus the visible and OCT light) as the index refraction affects the radius of curvature needed to provide a given focal length, which can affect the length of the GRIN fiber needed to output the visible light at an appropriate beam size. In some embodiments, the GRIN fiber provide different focusing properties for the different types of light, such that when the light that passes through the GRIN fiber is focused by the same element (e.g., ball lens) as the light that did not pass through the GRIN fiber the light emitted by the focusing element has different properties. For example, the GRIN fiber can reduce the numerical aperture for the visible light and facilitate extension of the depth of focus for the visible light. As another example, the GRIN fiber can cause the visible light to have an increased depth of focus (e.g., an eight fold increase in the depth of focus that can be achieved for visible light), which can cause the visible light to impinge the surface of the sample with much larger spot size. This can facilitate color imaging with a resolution appropriate for generating visible light images comparable to images captured by a conventional digital camera, while facilitating OCT imaging with a resolution appropriate for microscopic imaging of the internal structure of the sample. In some embodiments, light (both visible light and OCT light) reflected by the sample can be focused by the ball lens, and OCT light can be returned to a OCT detector(s) (e.g., OCT detector(s) 214) via the single mode fiber, while a cladding of the dual clad fiber can be used to return light to a visible light detector(s) (e.g., visible light detector(s) 204).

In some embodiments, a spacer 310 can be disposed between ball lens 302 and the fibers (e.g., single mode fiber 304, and dual clad fiber 306/GRIN fiber 308). In some embodiments, spacer 310 can have any suitable diameter, and can allow beams of the OCT light and visible light to expand, which can facilitate an increase in the depth of focus. For example, spacer 310 an have a diameter in the range of about 0.1 to 5,000 μm, which can remain constant over the length of the spacer or can change along the length of the spacer (e.g., the diameter of the spacer can increase from a proximal end optically coupled to the fibers to a distal end optically coupled to/forming part of the focusing element). In a more particular example, the spacer can have a diameter of about 1 mm. As another example, ball lens 302 can have a diameter in the range of about 0.5 to 5 mm. In a more particular example, ball lens 302 can have a diameter of about 2.5 mm. Note that, one or both beams may be at least slightly off axis with respect to the optical axis of spacer 310 and/or ball lens 302. For example, single mode fiber 304 can be located on axis, while dual clad fiber/GRIN fiber 308 can be located slightly off axis. However, any negative effects can be mitigated, for example by a relatively low numerical aperture of the visible light optics. As another example, any positional errors caused by the fiber(s) being off axis remain consistent during scanning and accordingly can have a relatively small effect on the accuracy of the visible light and/or OCT image data.

FIG. 3B shows an example of optical components that can be used to focus light from an OCT light source and a visible light source at a similar focal length implemented in accordance with some embodiments of the disclosed subject matter. As shown in FIG. 3B, a ball lens and spacer were implemented and optically coupled to a tether that included a single mode fiber, a dual clad fiber, and a GRIN fiber disposed between the spacer and the dual clad fiber (e.g. as shown diagrammatically in FIGS. 3A and 3C).

Figure 3D:
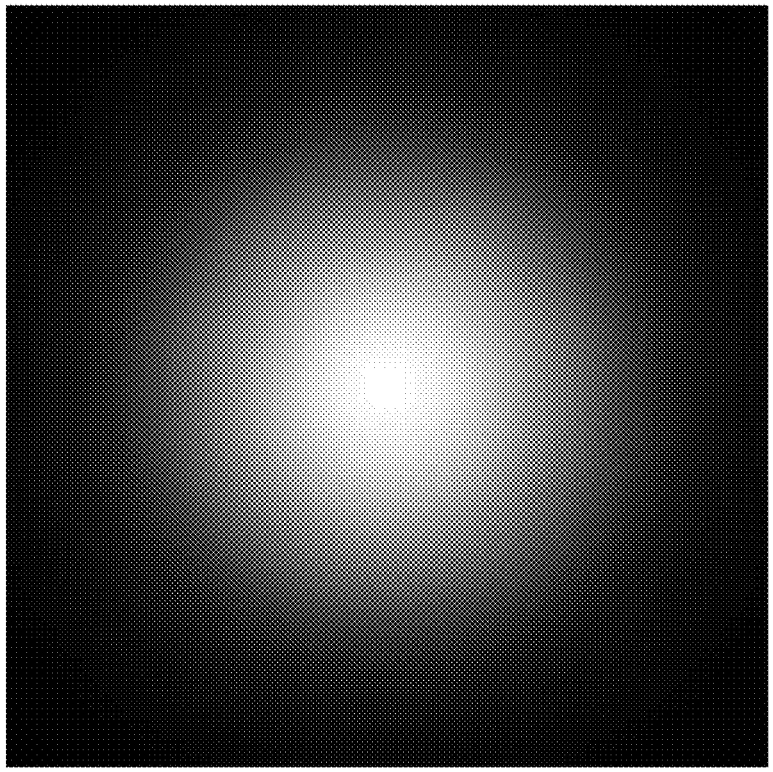
FIG. 3D shows different spot sizes for OCT light and visible light that can illuminate the sample in accordance with some embodiments of the disclosed subject matter.
Figure 3D:
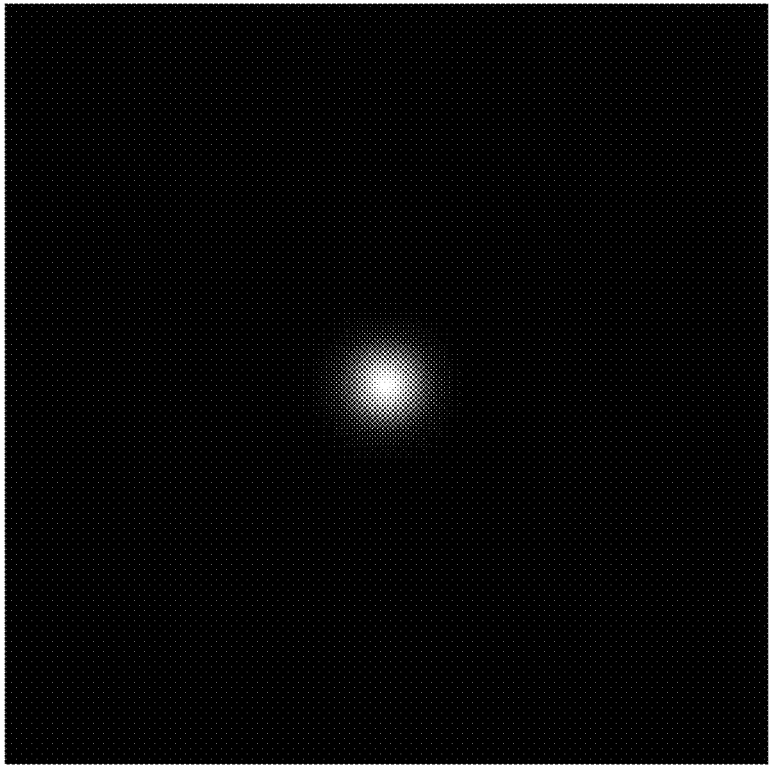

FIG. 3C shows an example simulation of optical paths of light from an OCT light source and a visible light source emitted from optics implemented in accordance with some embodiments of the disclosed subject matter. As shown in the simulation, the OCT light may initially have a wider beam than the visible light, but the focal point at can be located roughly the same distance from the ball lens, and the more aggressive focusing provided father from the optical axis of ball lens 302 can cause the OCT beam to have a narrower beam (and a smaller depth of focus) when it reaches the focal point (e.g., at or near the surface of the sample). As described below, FIG. 3D shows an example of different spot sizes at the focal point for OCT light and visible light, which can provide different lateral resolution (e.g., a more detailed microscopic resolution for the OCT light and a less detailed more macroscopic resolution for the visible light).

Figure 4A:
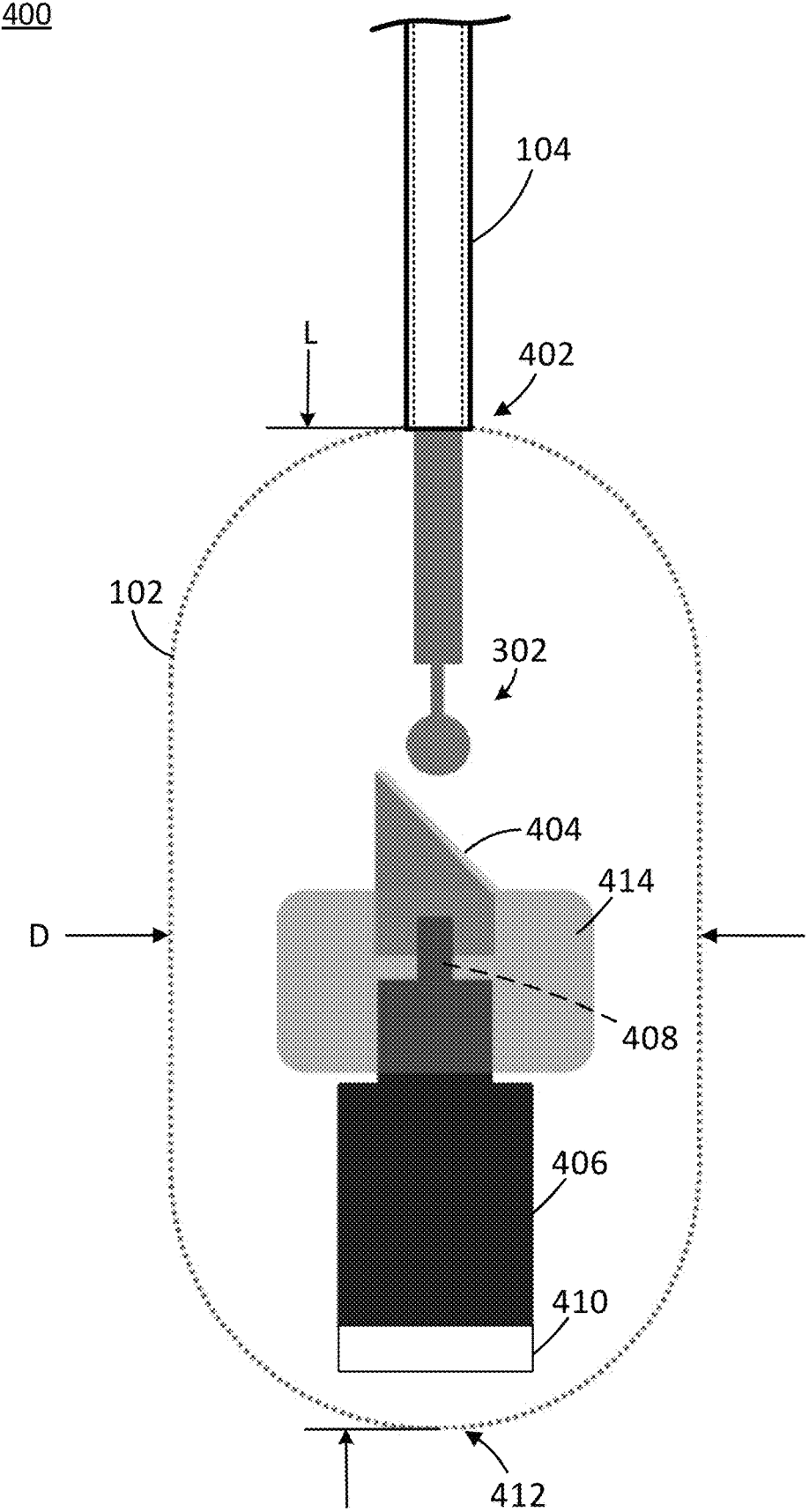
FIG. 4A shows an example of a tethered optical imaging probe that can be used in connection with systems for capsule-based multimode endoscopy in accordance with some embodiments of the disclosed subject matter.

FIG. 4A shows an example 400 of a tethered optical imaging probe that can be used in connection with systems for capsule-based multimode endoscopy in accordance with some embodiments of the disclosed subject matter. As shown in FIG. 4A, imaging probe 400 can include a capsule 102 and a tether 104 coupled to a proximal end 402 of capsule 102. In some embodiments, capsule 102 can have dimensions that facilitate swallowing by a subject, which can be in certain cases, be a human subject such as an adult or a child, and which can be in other cases, a veterinary subject. In some embodiments, capsule 102 can define a generally cylindrical shape with hemispherical ends with a capsule diameter D and a capsule length L. For example, the capsule diameter D can be between approximately 5 mm and approximately 20 mm. As another example, the capsule diameter D can be between approximately 10 mm and approximately 15 mm. As yet another example, the capsule length L can be between approximately 20 mm and approximately 30 mm. As still another example, the capsule length L can be between approximately 22 mm and approximately 28 mm.

In some embodiments, capsule 102 can be fabricated from a biocompatible material configured to efficiently transmit light reflected from a reflective surface 404 through capsule 102 onto a sample, and to efficiently transmit light reflected from the sample through capsule 102 onto the reflective surface 404. In some non-limiting examples, capsule 102 can be fabricated from PMMA in combination with other plastics or metals such as stainless steel or brass.

In some embodiments, tether 104 can include optical waveguides 108 and 112 (e.g., single mode fiber 304 and dual clad fiber 306). Additionally, in some embodiments, the configuration of the tethered optical imaging probe 400 can negate the need to rotate the optics within tether 104. For example, tether 104 can define a substantially reduced diameter when compared to a sheath used with other technique, and does not need to be fabricated from low-friction materials to compensate for a rotating optical fiber. Accordingly, tether 104 can provide more flexibility and a substantially reduced cost (e.g., on the order of a few cents to a few dollars compared to ~$200 when compared to a tether used with some rotating optical fiber-based techniques). In some embodiments, tether 104 can be fabricated from a biocompatible material (e.g., Polyimide, Pebax, PTFE, FEP).

In some embodiments, a motor 406 can be mechanically coupled to reflective surface 404, and both can be enclosed within capsule 104. In some embodiments, motor 406 can include a drive shaft 408 that rotatably couples reflective surface 404 to motor 406. In operation, as motor 406 rotates drive shaft 408, reflective surface 404 rotates with drive shaft 408. In the example shown in FIG. 4A, motor 406 can be powered by a power supply 410 arranged within capsule 102 near a distal end 412 of capsule. In some embodiments, power supply 410 can be implemented as a battery, a rechargeable battery, a solar cell, and/or any other suitable power supply components or combination of power supply components. In some embodiments, a controller (not shown) can be configured to wirelessly communicate with motor 406.

In some embodiments, motor 406 can be arranged within capsule 104 such that drive shaft 408 extends toward distal end 402 of capsule 102, thereby arranging the reflective surface 404 rotatably coupled thereto adjacent to ball lens 302. In some embodiments, motor 404 utilized in the tethered optical imaging probe 400 can be disposable and low-cost (e.g., between ~$1 and $10). For example, motor 404 can be a motor typically used to generate vibrations in a mobile device such as a smartphone. Techniques for controlling such a low-cost motor are described in U.S. Patent Application Publication No. 2018/0160965, which is hereby incorporated by reference herein in its entirety.

In some embodiments, drive shaft 408 of motor 406 can be associated with a damping weight 414 coupled thereto for rotation therewith, which can reduce short-term fluctuations in a rotational speed of motor 406 by increasing a moment of inertia. Additionally, in some embodiments, damping weight 414 can define a generally cylindrical shape, and can be made from any suitable material or combination of materials (e.g., brass). For example, damping weight 414 can define a weight of between approximately 0.01 grams (g) and 4 g.

Figure 4B:
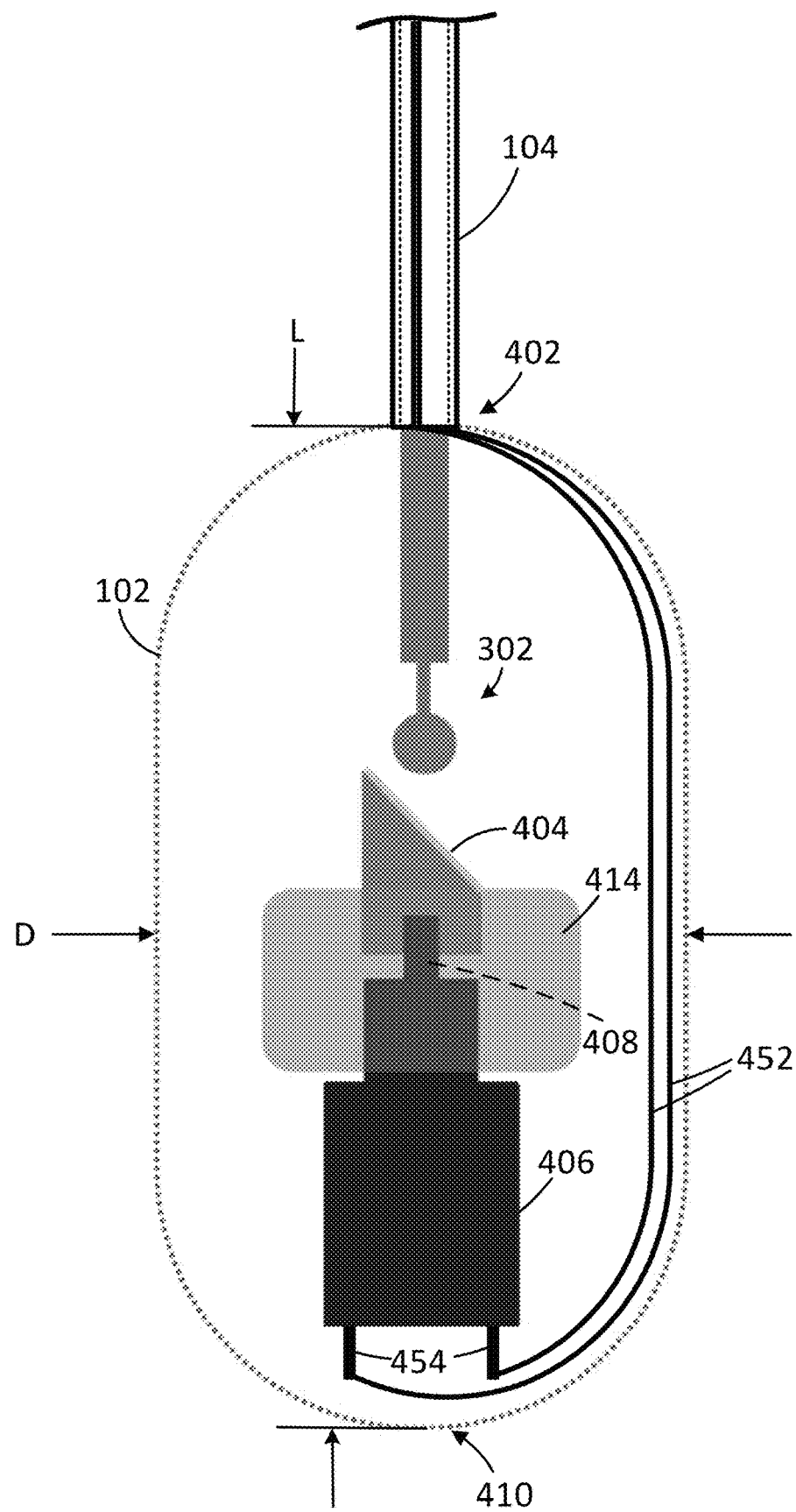
FIG. 4B shows another example of a tethered optical imaging probe that can be used in connection with systems for capsule-based multimode endoscopy in accordance with some embodiments of the disclosed subject matter.

FIG. 4B shows another example 450 of a tethered optical imaging probe that can be used in connection with systems for capsule-based multimode endoscopy in accordance with some embodiments of the disclosed subject matter. In some embodiments, tethered optical imaging probe 450 can be similar to tethered optical imaging probe 400 of FIG. 4A, but can be implemented using one or more wires that pass through tether 104. As shown in FIG. 4B, tethered optical imaging probe 450 includes one or more wires 452 extending into and along capsule 102. Each of the wires 452 can be coupled to a corresponding terminal 454 of motor 406.

In some embodiments, a power supply can be arranged externally from capsule 102, and the power supply can be in communication with a controller. For example, the controller can be in wired or wireless communication with the power supply, and/or the controller can include an integrated power supply.

Figure 4C:
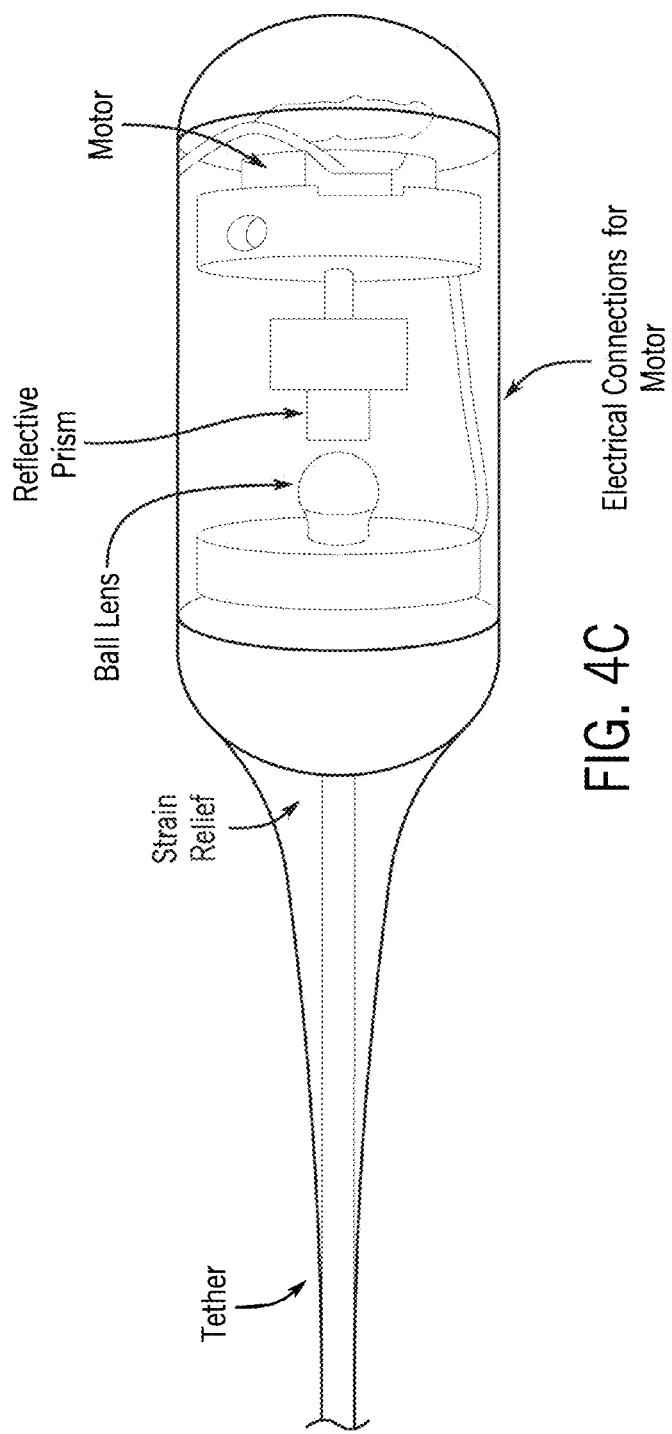
FIG. 4C shows an example of a tethered optical imaging probe implemented in accordance with some embodiments of the disclosed subject matter.

FIG. 4C shows an example of a tethered optical imaging probe implemented in accordance with some embodiments of the disclosed subject matter. As shown in FIG. 4C, a tethered capsule was implemented that incorporated optics similar to the optics shown in FIG. 3A in a capsule having a wired motor that controls rotation of a reflector (e.g., a reflective prism).

Figure 5:
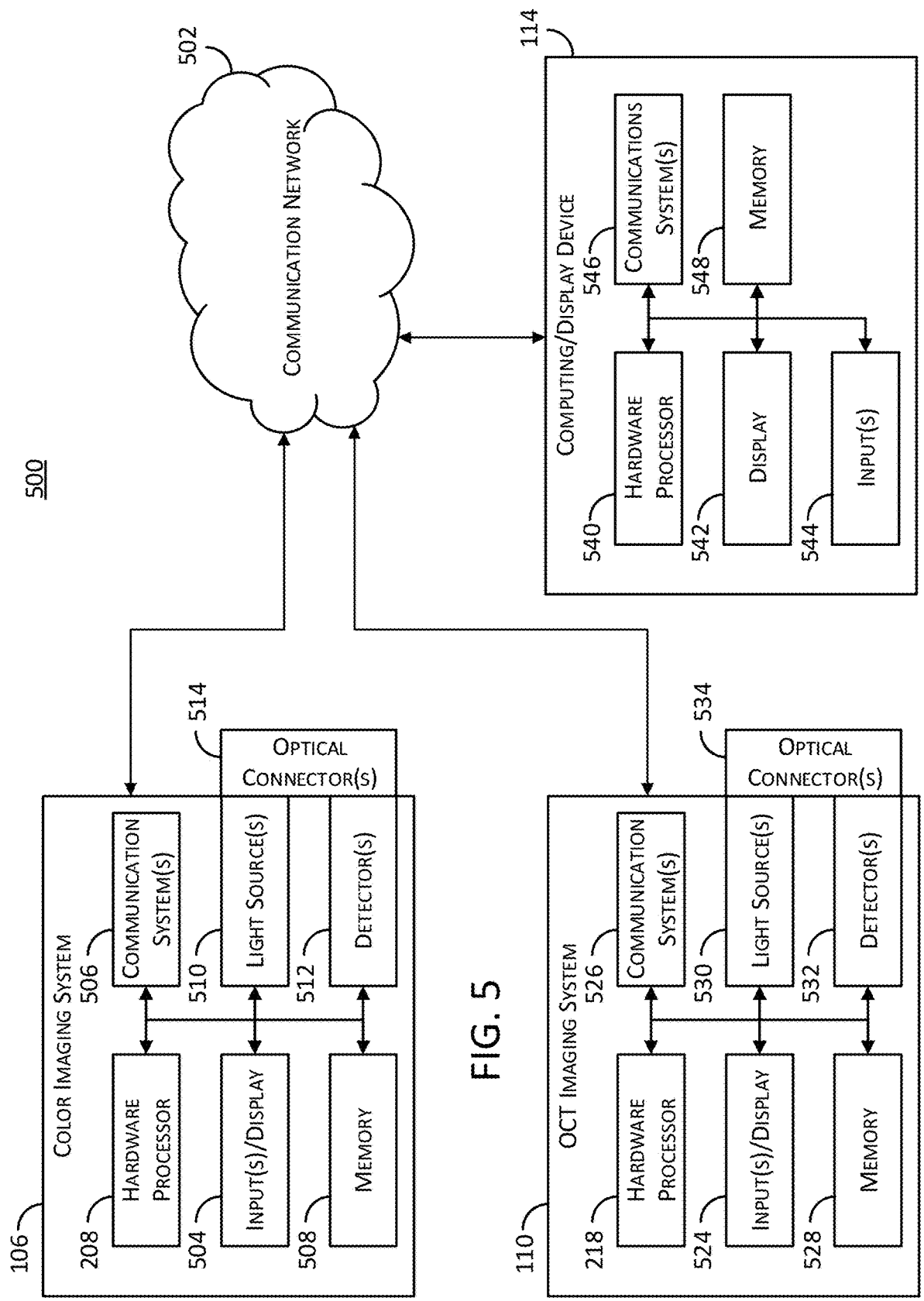
FIG. 5 shows an example of hardware that can be used to implement a visible light imaging device, an OCT imaging device, and/or a computing device that can be used in connection with some embodiments of mechanisms for capsule-based multimode endoscopy in accordance with some embodiments of the disclosed subject matter.

FIG. 5 shows an example 500 of hardware that can be used to implement a visible light imaging device, an OCT imaging device, and/or a computing device that can be used in connection with some embodiments of mechanisms for capsule-based multimode endoscopy in accordance with some embodiments of the disclosed subject matter. For example, hardware shown in FIG. 5 can be used to implement at least a portion of system 100. As shown in FIG. 5, in some embodiments, a color imaging system (e.g., visible light imaging device 106) can include a hardware processor 208, a user interface and/or display 504, one or more communication systems 506, memory 508, one or more visible light sources 510, one or more electromagnetic detectors 512, and/or one or more optical connectors 514. In some embodiments, hardware processor 208 can be any suitable hardware processor or combination of processors, such as a central processing unit (CPU), a graphics processing unit (GPU), a microcontroller (MCU), an FPGA, an ASIC, a dedicated image processor, etc. In some embodiments, input(s) and/or display 504 can include any suitable display device(s), such as a computer monitor, a touchscreen, a television, a transparent or semitransparent display, a head mounted display, etc., and/or input devices and/or sensors that can be used to receive user input, such as a keyboard, a mouse, a touchscreen, a microphone, a gaze tracking system, motion sensors, etc. Note that, in some embodiments, input(s)/display 504 can be omitted, such as embodiments in which operations of color imaging system 110 is controlled by computing device 114.

In some embodiments, communications systems 506 can include any suitable hardware, firmware, and/or software for communicating information over a communication network 502 and/or any other suitable communication networks. For example, communications systems 506 can include one or more transceivers, one or more communication chips and/or chip sets, etc. In a more particular example, communications systems 506 can include hardware, firmware and/or software that can be used to establish a Wi-Fi connection, a Bluetooth connection, a cellular connection, an Ethernet connection, an optical connection, etc.

In some embodiments, communication network 502 can be any suitable communication network or combination of communication networks. For example, communication network 502 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, etc. In some embodiments, communication network 502 can be a local area network, a wide area network, a public network (e.g., the Internet), a private or semi-private network (e.g., a corporate or university intranet), any other suitable type of network, or any suitable combination of networks. Communications links shown in FIG. 5 can each be any suitable communications link or combination of communications links, such as wired links, fiber optic links, Wi-Fi links, Bluetooth links, cellular links, etc.

In some embodiments, memory 508 can include any suitable storage device or devices that can be used to store instructions, values, etc., that can be used, for example, by hardware processor 208 to process image data generated by one or more optical detectors, to present content using input(s)/display 504, to communicate with computing device 114 via communications system(s) 506, etc. Memory 508 can include any suitable volatile memory, non-volatile memory, storage, any other suitable type of storage medium, or any suitable combination thereof. For example, memory 508 can include RAM, ROM, EEPROM, one or more flash drives, one or more hard disks, one or more solid state drives, one or more optical drives, etc. In some embodiments, memory 508 can have encoded thereon a computer program for controlling operation of color imaging system 106. In some such embodiments, hardware processor 208 can execute at least a portion of the computer program to control one or more light sources and/or detectors (e.g., to capture visible light image data as described above in connection with FIG. 2), to generate images and/or calculate values (e.g., a visible light image, etc.), transmit and/or receive information to/from computing device 114, combine visible light images from different color channels to generate multi-colored images, etc.

In some embodiments, imaging system 106 can include one or more light sources 510, such one or more coherent or incoherent light sources (e.g., light emitting diodes or combination of light emitting diodes, a white light source, etc.), which can be broadband light sources, and/or narrower band light sources. For example, the bandwidth of the light source can be selected to provide a range of wavelengths that facilitates color imaging at desired wavelengths. Additionally, in some embodiments, light sources 510 can be associated with one or more filters.

In some embodiments, imaging system 106 can include one or more light detectors 512, such as one or more photodiodes, and/or one or more image sensors (e.g., a CCD image sensor or a CMOS image sensor, either of which may be a single pixel, a linear array, or a two-dimensional array). For example, in some embodiments, detectors 512 can include one or more detectors configured to detect light at specific wavelengths (e.g., using filters, using optics to guide light of different wavelengths to different portions of the detector(s), etc.)

In some embodiments, imaging system 106 can include one or more optical connectors 514. For example, such optical connectors can be fiber optic connectors configured to form an optical connection between light source(s) 510 and/or detector 512 and an optical fiber (e.g., as part of a fiber optic cable), such as the dual-clad fiber and multimode fiber shown in FIG. 2.

In some embodiments, an OCT imaging system (e.g., OCT imaging device 110) can include a hardware processor 218, a user interface and/or display 524, one or more communication systems 526, memory 528, one or more OCT light sources 530, one or more electromagnetic detectors 532, and/or one or more optical connectors 534. In some embodiments, hardware processor 218 can be any suitable hardware processor or combination of processors, such as a CPU, a GPU, an MCU, an FPGA, an ASIC, a dedicated image processor, etc. In some embodiments, input(s) and/or display 524 can include any suitable display device(s), such as a computer monitor, a touchscreen, a television, a transparent or semitransparent display, a head mounted display, etc., and/or input devices and/or sensors that can be used to receive user input, such as a keyboard, a mouse, a touchscreen, a microphone, a gaze tracking system, motion sensors, etc. Note that, in some embodiments, input(s)/display 524 can be omitted, such as embodiments in which operations of OCT imaging system 110 is controlled by computing device 114.

In some embodiments, communications systems 526 can include any suitable hardware, firmware, and/or software for communicating information over a communication network 502 and/or any other suitable communication networks. For example, communications systems 526 can include one or more transceivers, one or more communication chips and/or chip sets, etc. In a more particular example, communications systems 526 can include hardware, firmware and/or software that can be used to establish a Wi-Fi connection, a Bluetooth connection, a cellular connection, an Ethernet connection, an optical connection, etc.

In some embodiments, memory 528 can include any suitable storage device or devices that can be used to store instructions, values, etc., that can be used, for example, by hardware processor 218 to process image data generated by one or more optical detectors, to present content using input(s)/display 524, to communicate with computing device 114 via communications system(s) 526, etc. Memory 528 can include any suitable volatile memory, non-volatile memory, storage, any other suitable type of storage medium, or any suitable combination thereof. For example, memory 528 can include RAM, ROM, EEPROM, one or more flash drives, one or more hard disks, one or more solid state drives, one or more optical drives, etc. In some embodiments, memory 528 can have encoded thereon a computer program for controlling operation of OCT imaging system 110. In some such embodiments, hardware processor 218 can execute at least a portion of the computer program to control one or more light sources and/or detectors (e.g., to capture OCT data), to generate images and/or calculate values (e.g., an OCT image, etc.), transmit and/or receive information to/from computing device 114, combine OCT images from different channels and/or times to generate merged OCT images, etc.

In some embodiments, OCT imaging system 110 can include one or more light sources 530, such as a coherent or incoherent light source (e.g., a light emitting diode or combination of light emitting diodes, a white light source, etc.), which can be a broadband light source, or a narrower band light source. For example, the bandwidth of the light source can be selected to provide a range of wavelengths that facilitates depth detection over a maximum imaging range of OCT imaging system 110. Additionally, in some embodiments, light sources 530 can be associated with one or more filters.

In some embodiments, OCT imaging system 110 can include one or more light detectors 532, such as one or more photodiodes, and/or one or more image sensors (e.g., a CCD image sensor or a CMOS image sensor, either of which may be a single pixel, a linear array, or a two-dimensional array). For example, in some embodiments, detectors 532 can include one or more detectors configured to detect light at specific wavelengths (e.g., using filters, using optics to guide light of different wavelengths to different portions of the detector(s), etc.)

In some embodiments, OCT imaging system 110 can include one or more optical connectors 534. For example, such optical connectors can be fiber optic connectors configured to form an optical connection between light source(s) 530 and/or detector(s) 532 and an optical fiber (e.g., as part of a fiber optic cable).

In some embodiments, computing device 114 can include a hardware processor 540, a display 542, one or more inputs 544, one or more communication systems 546, and/or memory 548. In some embodiments, hardware processor 540 can be any suitable hardware processor or combination of processors, such as a CPU, a GPU, an MCU, an FPGA, an ASIC, a dedicated image processor, etc. In some embodiments, display 542 can include any suitable display devices, such as a computer monitor, a touchscreen, a television, a transparent or semitransparent display, a head mounted display, etc. In some embodiments, inputs 544 can include any suitable input devices and/or sensors that can be used to receive user input, such as a keyboard, a mouse, a touchscreen, a microphone, a gaze tracking system, motion sensors, etc.

In some embodiments, communications systems 546 can include any suitable hardware, firmware, and/or software for communicating information over communication network 502 and/or any other suitable communication networks. For example, communications systems 546 can include one or more transceivers, one or more communication chips and/or chip sets, etc. In a more particular example, communications systems 546 can include hardware, firmware and/or software that can be used to establish a Wi-Fi connection, a Bluetooth connection, a cellular connection, an Ethernet connection, etc.

In some embodiments, memory 548 can include any suitable storage device or devices that can be used to store instructions, values, etc., that can be used, for example, by hardware processor 540 to present content using display 542, to communication with one or more imaging devices, etc. Memory 548 can include any suitable volatile memory, non-volatile memory, storage, any other suitable type of storage medium, or any suitable combination thereof. For example, memory 548 can include RAM, ROM, EEPROM, one or more flash drives, one or more hard disks, one or more solid state drives, one or more optical drives, etc. In some embodiments, memory 548 can have encoded thereon a computer program for controlling operation of computing device 114. In such embodiments, hardware processor 540 can execute at least a portion of the computer program to receive content (e.g., visible light image data, OCT data) from one or more imaging devices (e.g., color imaging device 106, OCT imaging device 110), co-register visible light image data and OCT image data, present content (e.g., images and/or values), transmit content to one or more other computing devices and/or imaging systems, etc.

In some embodiments, computing device 114 can be any suitable computing device, such as a general purpose computer or special purpose computer. For example, in some embodiments, computing device 114 can be a smartphone, a wearable computer, a tablet computer, a laptop computer, a personal computer, a server, etc. As another example, in some embodiments, computing device 114 can be a medical device or a portion of a medical device, a system controller, etc.

Figure 6:
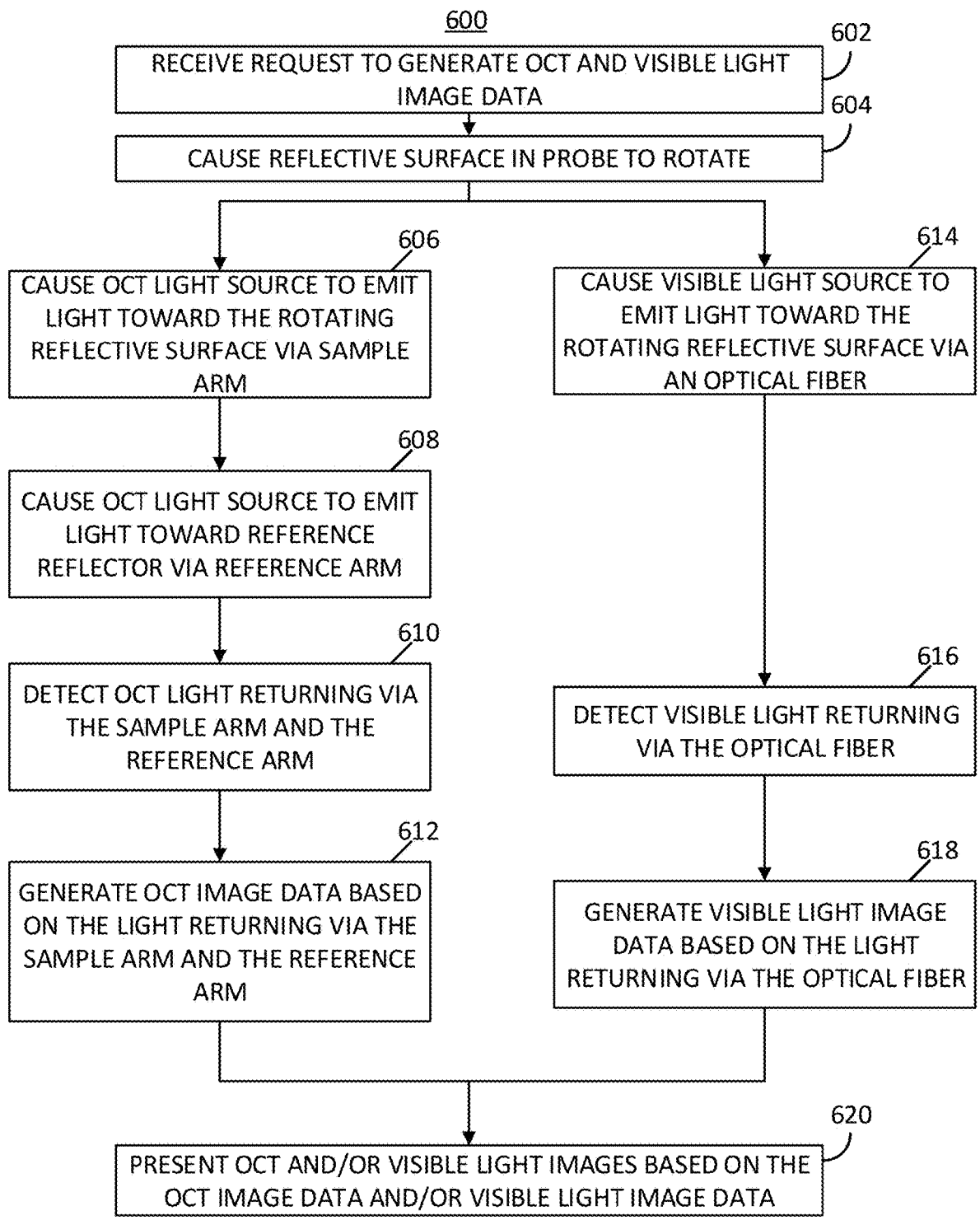
FIG. 6 shows an example of a process for generating multimode image data in accordance with some embodiments of the disclosed subject matter.

FIG. 6 shows an example 600 of a process for generating multimode image data in accordance with some embodiments of the disclosed subject matter. As shown in FIG. 6, at 602, process 600 can receive a request to generate OCT data and visible light image data. In some embodiments, the request can be received using any suitable technique or combination of techniques. For example, such a request can be received via input to a user interface (e.g., presented by computing device 114, visible light imaging device 106, and/or OCT imaging device 110). As another example, such a request can be received via actuation of a switch (e.g., a physical switch that initiates imaging, a software switch that initiates imaging, a combination of keystrokes on a keyboard that initiates imagining, etc.).

At 604, process 600 can cause a reflective surface in a probe to begin rotating (e.g., in anticipation of image data being captured). In some embodiments, process 600 can cause the reflective surface to rotate using any suitable technique or combination of techniques. For example, as described above in connection with FIGS. 4A and 4B, process 600 can cause a motor within a capsule to begin rotating, thereby causing a reflective surface that is mechanically coupled to the motor to begin rotating.

At 606, process 600 can cause an OCT light source to emit light toward the rotating reflective surface via a sample arm of an OCT imaging system. In some embodiments, process 600 can use any suitable components to cause the light to be emitted toward the reflective surface. For example, as described above in connection with FIG. 2, process 600 can cause light to be emitted from an OCT light source toward a single mode fiber that is coupled to the probe via a beam splitter and an optical circulator.

At 608, process 600 can cause an OCT light source to emit light toward a reference reflector via a reference arm of the OCT imaging system. In some embodiments, process 600 can use any suitable components to cause the light to be emitted toward the reflective surface. For example, as described above in connection with FIG. 2, process 600 can cause light to be emitted from an OCT light source toward a single mode fiber that is coupled to the reference reflector via the beam splitter and another optical circulator.

At 610, process 600 can detect light returning via the sample arm and the reference arm to generate OCT data. In some embodiments, process 600 can use any suitable technique or combination of techniques to generate OCT data using the returning light from the sample arm and the reference arm. For example, as described above in connection with FIG. 2, light from the two arms can interfere at an optical component such as a beam splitter, and interference between the two signals can be detected.

At 612, process 600 can generate OCT image data in real time based on light returning via the sample arm and the reference arm. In some embodiments, process 600 can use any suitable technique or combination of techniques to generate OCT image data. For example, based on the interference pattern(s) detected at 610, process 600 can generate A-line data indicative of the structure of the sample along the axial direction (e.g., along an axis extending substantially normal to a surface of the capsule) at a particular lateral location within the sample being imaged.

At 614, process 600 can cause a visible light source to emit light toward the rotating reflective surface. In some embodiments, process 600 can use any suitable components to cause the visible light to be emitted toward the reflective surface. For example, as described above in connection with FIG. 2, process 600 can cause light to be emitted from a visible light source toward a dual clad fiber that is coupled to the probe via a dual clad fiber coupler and a GRIN fiber.

At 616, process 600 can detect visible light returning from the probe that has been reflected by the sample. In some embodiments, process 600 can use any suitable technique or combination of techniques to generate visible light image data using the returning light. For example, as described above in connection with FIG. 2, light returning from the probe can be emitted toward one or more visible light detectors that can determine an amount of one or more wavelengths of light that have been reflected by the sample.

At 618, process 600 can generate visible light image data in real time based on visible light returning from the probe. In some embodiments, process 600 can use any suitable technique or combination of techniques to generate OCT image data. For example, based on the light detected at 616, process 600 can generate color image data for one or more locations on a surface of the sample.

At 620, process 600 can present OCT and/or visible light images based on the OCT image data generated at 612 and/or the visible light image data generated at 618. In some embodiments, process 600 can present the image data using any suitable technique or combination of techniques. For example, process 600 can present OCT image data and visible light image data representing the same portion of the sample in a side-by-side fashion (e.g., as described below in connection with FIGS. 7B to 7D, 8A, and 8B). As another example, process 600 can present a composite of OCT image data and visible light image data. In a more particular example, process 600 can present an oblique angle of the sample with the visible light image data used to present a surface of the tissue, and the OCT image data used to present a structure of the sample below the surface of the tissue.

Figure 7A:
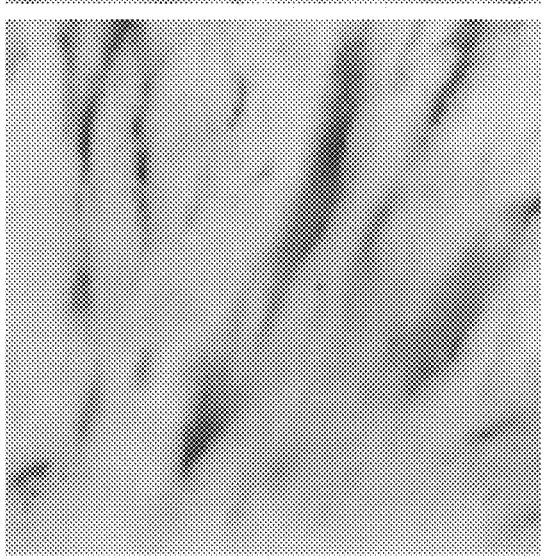
FIG. 7A shows an example of a visible light image captured ex vivo of swine mesenteric vessels generated using a conventional camera.

FIG. 7A shows an example of a visible light image captured ex vivo of swine mesenteric vessels generated using a conventional camera.

Figure 7B:
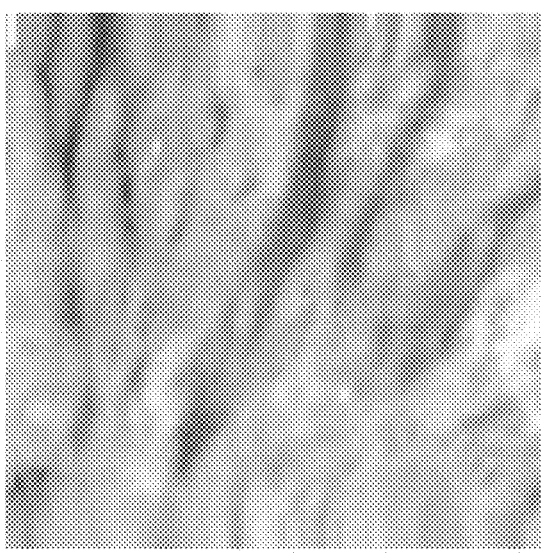
FIG. 7B shows an example of a visible light image captured ex vivo of swine mesenteric vessels generated using a capsule-based multimode endoscopy system implemented in accordance with some embodiments of the disclosed subject matter.
Figure 7C:
FIG. 7C shows an example of enface OCT image data captured ex vivo of swine mesenteric vessels generated using a capsule-based multimode endoscopy system implemented in accordance with some embodiments of the disclosed subject matter.

FIG. 7B shows an example of a visible light image captured ex vivo of swine mesenteric vessels generated using a capsule-based multimode endoscopy system implemented in accordance with some embodiments of the disclosed subject matter. As can be appreciated by a comparison of FIGS. 7A and 7B, the implemented capsule-based multimode endoscopy system (an image of which is shown in FIG. 4C) produced visible light image data that was of comparable or better quality than the conventional white light camera, while scanning individual points of the surface. FIG. 7C shows an example of enface OCT image data captured ex vivo of swine mesenteric vessels generated using a capsule-based multimode endoscopy system implemented in accordance with some embodiments of the disclosed subject matter. This shows the surface features that can be generated using OCT data alone, and lacks some of the details shown in FIG. 7B.

Figure 7D:
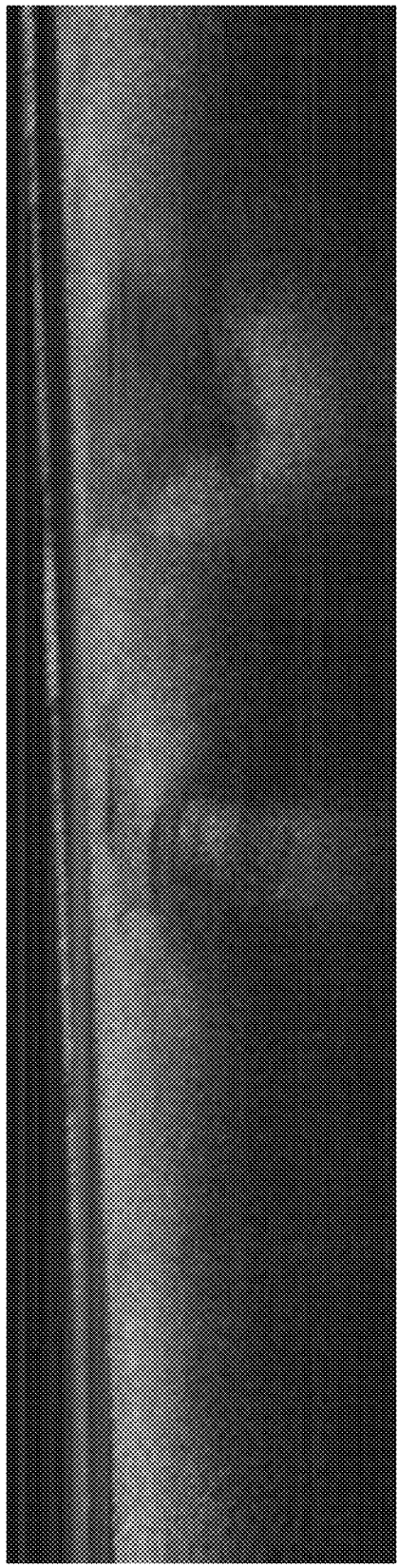
FIG. 7D shows an example of B-scan OCT image data captured ex vivo of swine mesenteric vessels generated using a capsule-based multimode endoscopy system implemented in accordance with some embodiments of the disclosed subject matter.

FIG. 7D shows an example of B-scan OCT image data captured ex vivo of swine mesenteric vessels generated using a capsule-based multimode endoscopy system implemented in accordance with some embodiments of the disclosed subject matter.

Figure 8B:
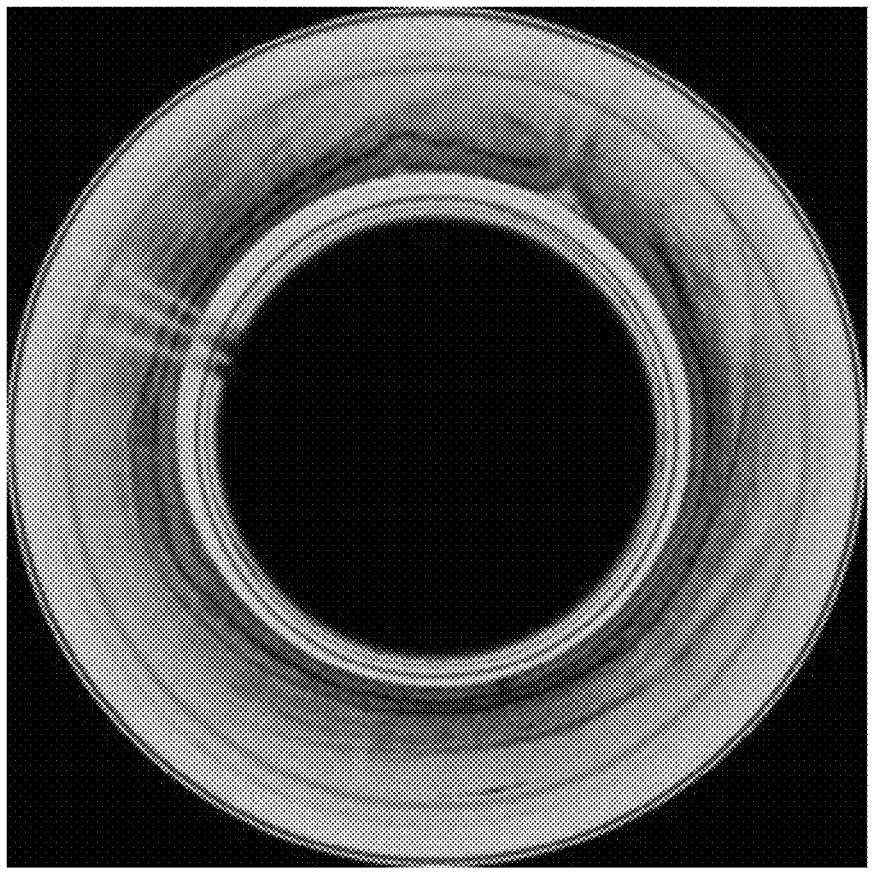
FIG. 8B shows an example of cross-sectional OCT image data captured in vivo of swine esophagus generated using a capsule-based multimode endoscopy system implemented in accordance with some embodiments of the disclosed subject matter.
Figure 8A:
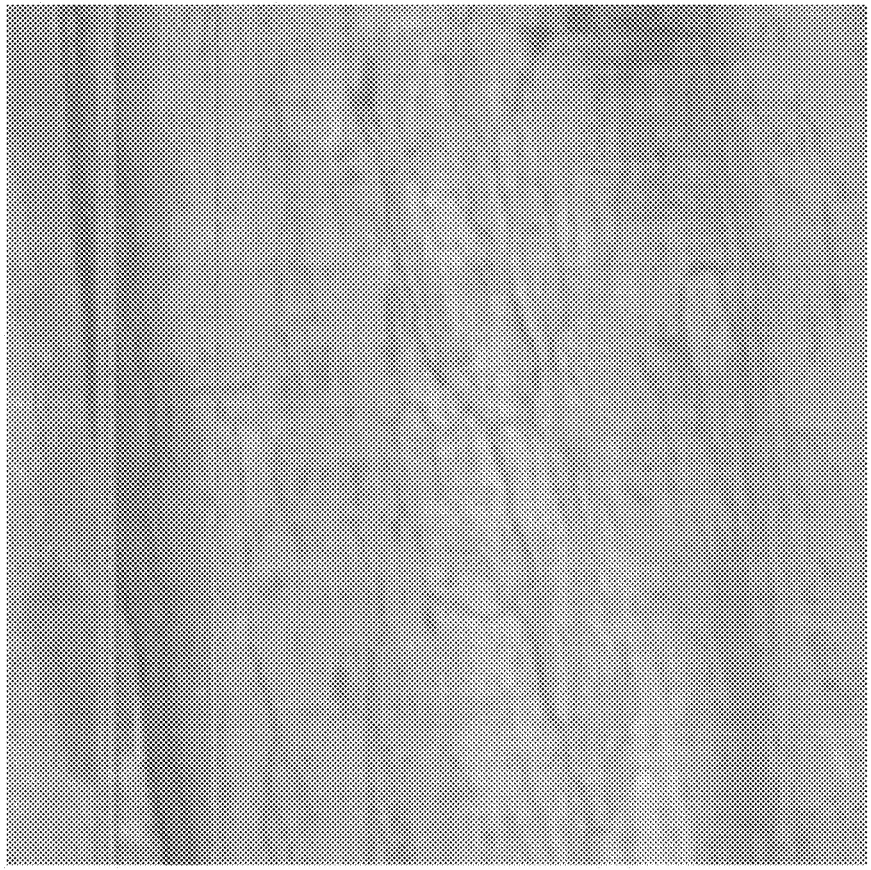
FIG. 8A shows an example of a visible light image captured in vivo of swine esophagus generated using a capsule-based multimode endoscopy system implemented in accordance with some embodiments of the disclosed subject matter.

FIGS. 8A and 8B show an example of a visible light image and cross-sectional OCT image data, respectively, captured in vivo of swine esophagus generated using a capsule-based multimode endoscopy system implemented in accordance with some embodiments of the disclosed subject matter. The implemented capsule was also used to image swine esophagus in vivo. The capsule was deployed in swine stomach using a modified endoscope which could hold and release the capsule at the distal tip, a step that is unnecessary in humans since an unsedated subject can typically swallow the capsule which will slide down to the stomach due to peristalsis. The swine esophagus was imaged using the implemented capsule-based multimode endoscopy system (an image of which is shown in FIG. 4C) by pulling back the capsule at a constant speed using a motorized pullback device while OCT and visible light image data was generated. In some embodiments, a constant pullback speed may be desirable, as it facilitates easier reconstruction of the tissue image in a correct form factor. Within the visible light image of FIG. 8A, blood vessels on the esophagus surface can be clearly identified, while in the OCT image different layers of esophagus can be observed.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RAM, Flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, any other suitable media that is fleeting and devoid of any semblance of permanence during transmission, and/or any suitable intangible media.

It will be appreciated by those skilled in the art that while the disclosed subject matter has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is hereby incorporated by reference, as if each such patent or publication were individually incorporated by reference herein.

Various features and advantages of the invention are set forth in the following claims.

What is claimed is:

1. A probe, comprising:
a rigid capsule;
a flexible tether coupled to a proximal end of the capsule;
a rotatable reflective surface disposed within the capsule;
a static first lens disposed within the capsule;
a first optical fiber optically coupled to the first lens,
the first optical fiber passing through the flexible tether;
a second optical fiber optically coupled to the first lens,
the second optical fiber passing through the flexible tether; and
a second lens disposed between a distal end of the second optical fiber and the first lens and not disposed between the first optical fiber and the first lens,
the second lens optically coupled to the second optical fiber and the first lens.

2. The probe of claim 1, wherein the rotatable reflective surface is configured to receive light emitted by the first lens and direct the light toward a circumference of the rigid capsule.

3. The probe of claim 1, further comprising a spacer disposed between the first lens and the second lens.

4. The probe of claim 1, wherein the first optical fiber is a single mode fiber that is configured to be optically coupled to an optical coherence tomography imaging system.

5. The probe of claim 4, wherein the second optical fiber is a dual clad fiber that is configured to be optically coupled to a visible light imaging system.

6. The probe of claim 1, further comprising a motor that is mechanically coupled to the rotatable reflective surface, and configured to rotate the rotatable reflective surface.

7. The probe of claim 1, wherein the first optical fiber is adjacent and parallel to the second optical fiber, and
wherein the first optical fiber and the second optical fiber are configured to couple to separate imaging systems.

8. The probe of claim 1, wherein the first lens comprises a ball lens.

9. The probe of claim 8, wherein the ball lens has an axial diameter of between 0.1 and 5 millimeters (mm).

10. The probe of claim 1, wherein the second lens comprises a graded index fiber.

11. The probe of claim 10, wherein the graded index fiber has a length of between 100 and 1,000 micrometers (μm).

12. The probe of claim 1, wherein a first electromagnetic radiation emitted from the first optical fiber is transmitted through the first lens to a sample, and
wherein a second electromagnetic radiation received from the sample is transmitted through the first lens and the second lens into the second optical fiber.

13. The probe of claim 1, wherein a first electromagnetic radiation emitted from the first optical fiber is transmitted through the first lens to a sample, and
wherein a second electromagnetic radiation emitted from the second optical fiber is transmitted through the second lens and the first lens.

14. A system for capsule-based multimode endoscopy, comprising:
a visible light imaging system comprising:
a visible light source; and
a visible light detector;
an optical coherence tomography (OCT) imaging system comprising:
an OCT light source;
an OCT detector;
a sample arm optically coupled to the OCT light source and the OCT detector; and
a reference arm optically coupled to the OCT light source and the OCT detector, the reference arm comprising a reference reflector; and
a probe comprising:
a rigid capsule;
a flexible tether coupled to a proximal end of the capsule;
a rotatable reflective surface disposed within the capsule;
a first lens disposed within the capsule;
a first optical fiber optically coupled to the first lens and the sample arm of the OCT imaging system,
the first optical fiber passing through the flexible tether;
a second optical fiber optically coupled to the first lens and the visible light imaging system, the second optical fiber passing through the flexible tether; and
a second lens disposed between a distal end of the second optical fiber and the first lens and not disposed between the first optical fiber and the first lens,
the second lens optically coupled to the second optical fiber and the first lens.

15. The system of claim 14, further comprising:
at least one processor that is programmed to:
cause the rotatable reflective surface to rotate;
cause the OCT light source to emit light toward the rotatable reflective surface via the first optical fiber;
cause the visible light source to emit light toward the rotatable reflective surface via the second optical fiber;
generate OCT data based on an interference between light reflected from a sample and light reflected from the reference reflector;
generate visible light image data based on light reflected from a surface of the sample; and
cause an image representing a first portion of the sample based on the OCT data to be presented simultaneously with an image representing the first portion of the sample based on the visible light image data.

16. The system of claim 14, wherein the rotatable reflective surface is configured to receive light emitted by the first lens and direct the light toward a circumference of the rigid capsule.

17. The system of claim 14, wherein the probe further comprises a spacer disposed between the first lens and the second lens.

18. The system of claim 14, wherein the first optical fiber is a single mode fiber.

19. The system of claim 18, wherein the second optical fiber is a dual clad fiber, and
wherein a core of the dual clad fiber is optically coupled to the visible light source and a cladding of the dual clad fiber is optically coupled to the visible light detector.

20. The system of claim 14, wherein the probe further comprises a motor that is mechanically coupled to the rotatable reflective surface, and configured to rotate the rotatable reflective surface.

21. The system of claim 14, wherein at least one of the first optical fiber or the second optical fiber is disposed off of a central axis of the first lens.

22. The system of claim 14, wherein the first optical fiber is disposed on a central axis of the first lens and the second optical fiber is disposed off of the central axis of the first lens.

23. The system of claim 14, wherein the first lens comprises a ball lens.

24. The system of claim 23, wherein the ball lens has an axial diameter of between 0.1 and 5 millimeters (mm).

25. The system of claim 14, wherein the second lens comprises a graded index fiber.

26. The system of claim 25, wherein the graded index fiber has a length of between 100 and 1,000 micrometers (μm).

27. The system of claim 14, wherein a first electromagnetic radiation emitted from the first optical fiber is transmitted through the first lens to a sample, and
wherein a second electromagnetic radiation received from the sample is transmitted through the first lens and the second lens into the second optical fiber.

28. The system of claim 14, wherein a first electromagnetic radiation emitted from the first optical fiber is transmitted through the first lens to a sample, and
wherein a second electromagnetic radiation emitted from the second optical fiber is transmitted through the second lens and the first lens.

* * * * *